United States Patent
Sumetsky

(10) Patent No.: US 7,684,658 B2
(45) Date of Patent: Mar. 23, 2010

(54) OPTIMIZED OPTICAL RESONATOR DEVICE FOR SENSING APPLICATIONS

(75) Inventor: Mikhail Sumetsky, Bridgewater, NJ (US)

(73) Assignee: OFS Fitel, LLC, Norcross, GA (US)

( * ) Notice: Subject to any disclaimer, the term of this patent is extended or adjusted under 35 U.S.C. 154(b) by 53 days.

(21) Appl. No.: 12/154,353

(22) Filed: May 22, 2008

(65) Prior Publication Data

US 2009/0010588 A1 Jan. 8, 2009

Related U.S. Application Data

(60) Provisional application No. 60/948,058, filed on Jul. 5, 2007.

(51) Int. Cl.
*G02B 6/00* (2006.01)
(52) U.S. Cl. ...................................... 385/12
(58) Field of Classification Search .................. 385/12
See application file for complete search history.

(56) References Cited

U.S. PATENT DOCUMENTS

| 7,587,105 B2* | 9/2009 | Ashkenazi et al. ............ 385/13 |
| 2004/0023396 A1* | 2/2004 | Boyd et al. ................. 435/872 |
| 2008/0180672 A1* | 7/2008 | Sigalas et al. ............... 356/432 |

OTHER PUBLICATIONS

Savchenkov et al., Optical resonators with ten million finesse, May 28, 2007, Optics Express, vol. 15 No. 11, pp. 6768-6773.*

* cited by examiner

*Primary Examiner*—Sarah Song

(57) ABSTRACT

An optical resonator is configured for optimized performance as a sensor by maximizing the slope and/or sharpness of the resonance peak, instead of maximizing the Q-factor of the resonator. These characteristics of the resonance peak are controlled, in accordance with the present invention, by modifying the physical parameters of the resonator structure (e.g., dimensions, spacing between waveguides, ring diameter, materials and associated refractive indices, etc.) until the desired peak attributes are achieved, regardless of the Q-factor associated with these optimum attributes.

9 Claims, 3 Drawing Sheets

OPTIMIZED OPTICAL RESONATOR DEVICE FOR SENSING APPLICATIONS

CROSS-REFERENCE TO RELATED APPLICATIONS

This application claims the benefit of U.S. Provisional Application No. 60/948,058, filed Jul. 5, 2007.

TECHNICAL FIELD

The present invention relates to an optical resonator configured for optimized performance as a sensor by maximizing the slope and sharpness of the resonance peak, instead of maximizing the Q-factor of the resonator.

BACKGROUND OF THE INVENTION

Electro-optic devices have shown great promise in sensor applications. Passive optical sensors offer safe and accurate operation in hostile environments of heat and temperature, while also being immune to electromagnetic interference. These advantages combine to make optically-based sensors attractive for a number of applications.

A resonant optical sensor is generally defined as a sensor based on optical resonators such as, for example, Fabry-Perot devices, spheres, rings, disks and the like, which are used as physical, chemical and/or biological sensors of the ambient medium. In most cases, the spectrum of the sensor consists of positive and/or negative resonant peaks. The sensor monitors changes in the tested "object" (e.g., ambient medium) by measuring and processing variations in the spectrum. U.S. Pat. No. 6,901,101 issued to R. L. Frick on May 31, 2005 is exemplary of this type of resonant optical sensor and includes an optical medium having a 'variable' cavity; that is, the cavity is physically altered in response to changes in a measurable parameter such as pressure, temperature, force, flow rate, etc. The cavity is disposed near or within a high Q optical resonator, where the variability of the cavity affects the resonance condition within the high Q resonator.

It is often necessary in arrangements such as disclosed by Frick to detect very small variations in the spectrum, comparable with or less than the dimensions of a resonant peak itself. Commonly, it is assumed that the higher the Q-factor of the resonator, the more sensitive the resonator is to changes in the refractive index (indeed, a very large Q-factor denotes an extremely narrow resonance in the transmission power spectrum). However, the maximum Q-factor of an individual resonance peak corresponds to a resonance peak with vanishing height, which is useless for sensing. Moreover, a resonance peak composed of several adjacent peaks may have a complex shape, for which the Q-factor cannot be easily determined.

Thus, a need remains for ascertaining a proper set of parameters that may be used to optimize the sensitivity of a resonant optical sensor.

SUMMARY OF THE INVENTION

The need remaining in the art is addressed by the present invention, which relates to an optical resonator configured for optimized performance as a sensor by maximizing the slope and/or sharpness of the resonance peak, instead of maximizing the Q-factor of the resonator.

In order to magnify the sensor's response (and therefore increase its accuracy), it has been determined that the resonant peak needs to be as sharp and/or as steep as possible. These characteristics of the resonance peak are controlled, in accordance with the present invention, by modifying the physical parameters of the resonator structure (e.g., dimensions, spacing between waveguides, ring diameter, refractive index contrast between the waveguide and the ring, refractive index of the separating medium, etc.) until the desired peak attributes are achieved, regardless of the Q-factor associated with these optimum attributes.

The characteristics of a resonant optical sensor depend on properties that can be categorized as either "intrinsic" parameters or "variable" parameters. Intrinsic parameters are those related to material properties of the system, such as waveguide composition, surface roughness and the like, which are not affected by the geometry of the resonator. Variable parameters are those which can be adjusted in the resonator design to alter the optical resonance, such as the dimensions of the resonator, the geometry of the resonator, and the various distances between the waveguides and the resonators.

In accordance with one embodiment of the present invention, using a single resonance (e.g., in a single ring resonator), it has been found that the Q-factor values associated sharpest peak are consistently $\frac{2}{3}Q_{int}$ (for transmission) and $\frac{3}{4}Q_{int}$ (for reflection), where $Q_{int}$ is defined as the intrinsic Q-factor associated with the intrinsic material properties of the resonator (neglecting the influence of coupling to input and output waveguides). Similarly, the Q-factor values for the steepest slope are consistently $\frac{1}{2}Q_{int}$ (for transmission) and $\frac{2}{3}Q_{int}$ (for reflection). Knowing these values, specific values for the variable parameters of the sensor design itself can be determined. Similar relations can be derived for sensors consisting of multiple resonators to determine the proper variable parameters. Thus, it is clear from the above that the maximum Q-factor does not produce a resonator with the greatest sensitivity.

Other and further aspects of the present invention will become apparent during the course of the following discussion and by reference to the accompanying drawings.

BRIEF DESCRIPTION OF THE DRAWINGS

Referring now to the drawings.

DETAILED DESCRIPTION

Figure 1:
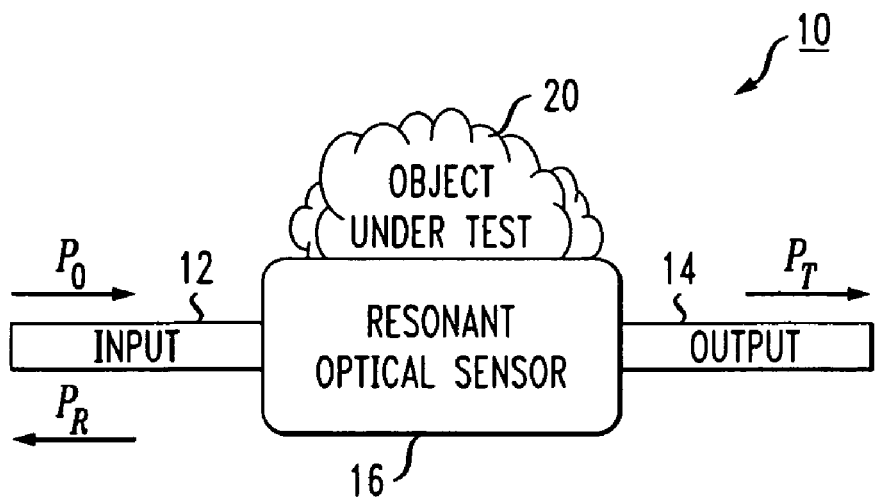
FIG. 1 contains a simplified block diagram of an exemplary environment within which an resonant optical sensor may be employed.

FIG. 1 contains a simplified block diagram of an exemplary resonant optical sensor 10. As shown, sensor 10 includes an input optical signal path 12, an output optical signal path 14 and an optically resonant sensing device 16 disposed therebetween. A hypothetical "object under test" 20 is disposed adjacent to sensing device 16. As discussed above, object 20 may simply be the ambient environment/medium in which sensor 10 is positioned, where (for example) sensor 10 may be used to detect the presence of certain contaminants in the atmosphere. The properties of any specific object under test are not germane to the purposes of the present invention. In this arrangement, a single waveguide may serve as both the input and output waveguide, and either the transmission spectrum or reflection spectrum may be absent, or of negligible optical power.

In use, an optical signal is coupled into input signal path 12 (denoted as $P_O$), where the spectrum of the transmitted signal is labeled as $P_T$ along output path 14. The spectrum of the reflected signal (propagating in the reverse direction along input signal path 12) is labeled as $P_R$ in FIG. 1. By virtue of incorporating a resonating optical structure (such as a "ring", Fabry-Perot cavity, or the like) in the signal path as optical resonant sensing device 16, the transmitted and reflected spectra will include one or more resonant peaks, at wavelengths that can be associated with properties of the object under test.

If is often necessary to detect very small variations in the spectrum, comparable with (or even less than) the dimensions of a resonant peak itself. In order to magnify the sensor's response and increase its accuracy, it is desirable to have the resonant peak as sharp and/or as steep as possible. In the past, it was presumed that the maximum Q-factor (i.e., narrowest peak) would always be preferred. However, for the largest possible Q-factor, the slope increases while the peak height approaches zero; clearly, these values make sensor applications useless. Furthermore, the FWHM of a resonant peak is restricted by the losses of the resonator itself. In fact, for a given wavelength $\lambda$, the FWHM of a resonant peak denoted $\Delta\lambda_{FWHM}$, cannot be less than $\lambda/Q_{int}$, where $Q_{int}$ is often dominated by the internal losses of the sensor.

In accordance with the present invention, therefore, it has been found that the sensitivity of a resonant optical sensor can be optimized by considering those factors which can be modified (physical parameters, device geometry, spacing between elements, materials (and associated refractive indicies) and the like)—the variable parameters. The "fixed" intrinsic parameters, such as the material composition and associated intrinsic loss, are not considered when determining the optimized sensitivity. By analyzing the relations governing the performance of the sensor, the proper values for the variable parameters can be determined in order to optimize the sensitivity by providing the maximum slope and sharpness of the resonant peaks. The maximum Q-factor is not a consideration.

Figure 2:
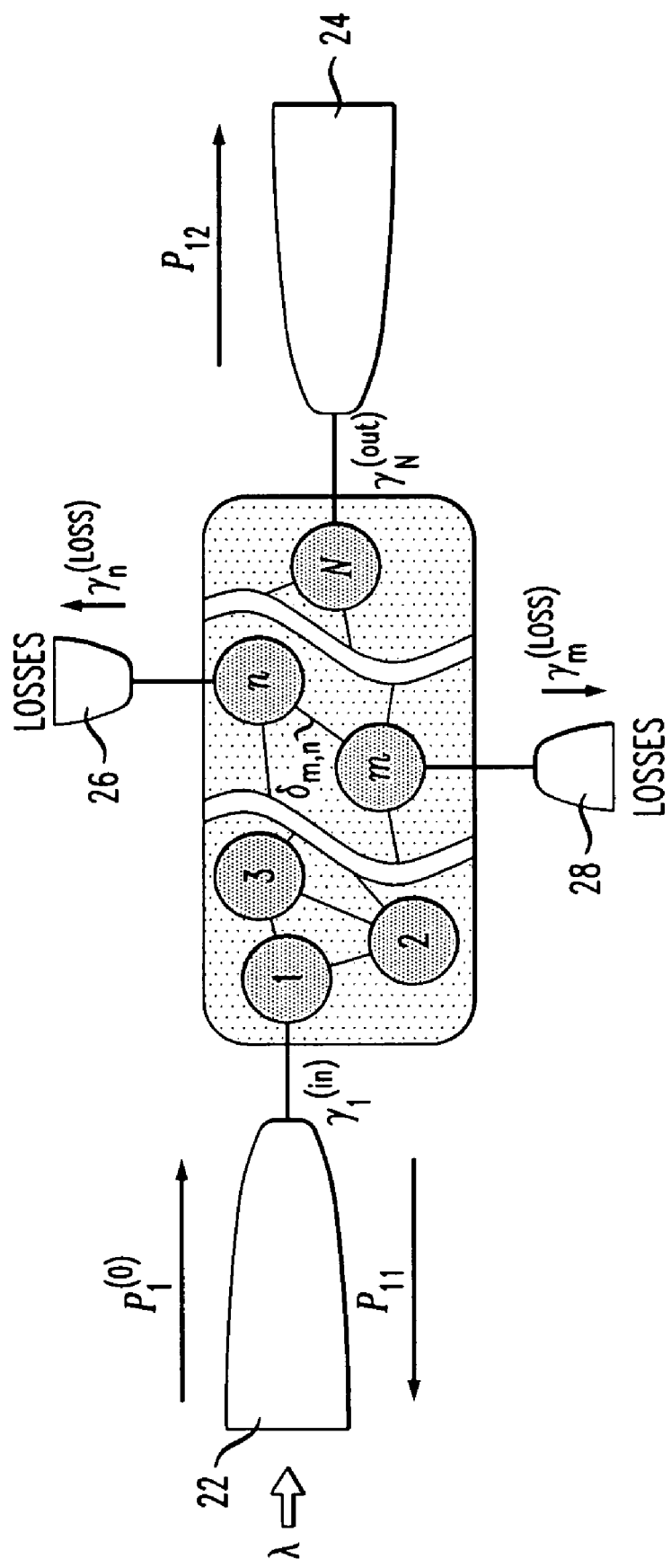
FIG. 2 is a model of a resonant optical sensor comprising a plurality of N elementary resonators.

FIG. 2 is an exemplary model of a resonant optical sensor comprising a plurality of N elementary optical resonators 20 coupled to each other (illustrated by the dark circles labeled "1", "2":, ... "m", "n", ... "N" in FIG. 2). An input waveguide 22 and an output waveguide 24 are as shown. The spectral resonances are formed by transmission of light through a single or a few adjacent eigenmodes of the resonator. The resonator is modeled as a plurality of single mode resonators with wavelength eigenvalues $\lambda_n$. The 'environment' within which the sensor is located is indicated by the dotted background behind resonators 20. Resonators 20 may be coupled to each other, and also to input waveguide 22 and output waveguide 24, in the manner shown. The coupling coefficient between resonators m and n is defined as $\delta_{mn}$, as shown in FIG. 2. The coupling of a resonator n to input or output waveguide 22/24 is defined by the coefficient $\gamma_n^{(in)}$ (for coupling to input waveguide 22) or $\gamma_n^{(out)}$ (for coupling to output waveguide 24). In the arrangement of FIG. 2, these values are shown as $\gamma_1^{(in)}$ and $\gamma_N^{(out)}$.

As mentioned above, the intrinsic losses of a resonant optical sensor are those losses which are generally fixed and associated with the materials forming the device. In the illustration of FIG. 2, these intrinsic losses are modeled by virtual output waveguides 26, 28. The coupling coefficients between resonators m and n and these 'virtual' output waveguides are denoted in FIG. 2 as $\gamma_m^{loss}$ and $\gamma_n^{loss}$, respectively. In accordance with the present invention, these coefficients are treated as fixed quantities which are not altered as part of the optimization. Hereafter, therefore, all such intrinsic losses will be defined as "$\gamma$"—a constant value that is fixed and unchanged.

The resonant transmission and reflection spectra of the generalized configuration of FIG. 2 can be calculated by the generalized Breit-Wigner formula, where in particular the resonant transmission power P from input waveguide 22 to output waveguide 24 is defined by the following:

$$P_{in,out} = P_{in}^{(0)} \sum_{m,n} \gamma_m^{in} \gamma_n^{out} |Q_{mn}|^2.$$

Here, $P_{in}^{(0)}$ is defined as the power input into output waveguide 24, where the sum is taken over the entire plurality of elemental resonators that couple to input waveguide 22 and output waveguide 24, and $$Q = \Lambda^{-1},$$

where $$\Lambda = \begin{pmatrix} \lambda - \lambda_1 + \frac{i}{2}\gamma_1 & \delta_{12} & \cdots & \delta_{1N} \\ \delta_{12} & \lambda - \lambda_2 + \frac{i}{2}\gamma_2 & \cdots & \delta_{2N} \\ \cdots & \cdots & \cdots & \cdots \\ \delta_{N1} & \delta_{N2} & \cdots & \lambda - \lambda_N + \frac{i}{2}\gamma_N \end{pmatrix}$$

The parameters $\gamma_1, \gamma_2, \ldots, \gamma_N$ determine the widths of the associated uncoupled eigenvalues $\lambda_1, \lambda_2, \ldots, \lambda_N$. The reflection power into input waveguide 22, denoted $P_{in,in}$ can be found from the power conservation law:

$$P_{in,in} = P_{in}^{(in)} - \sum_{out \neq in} P_{in,out}.$$

Figure 3:
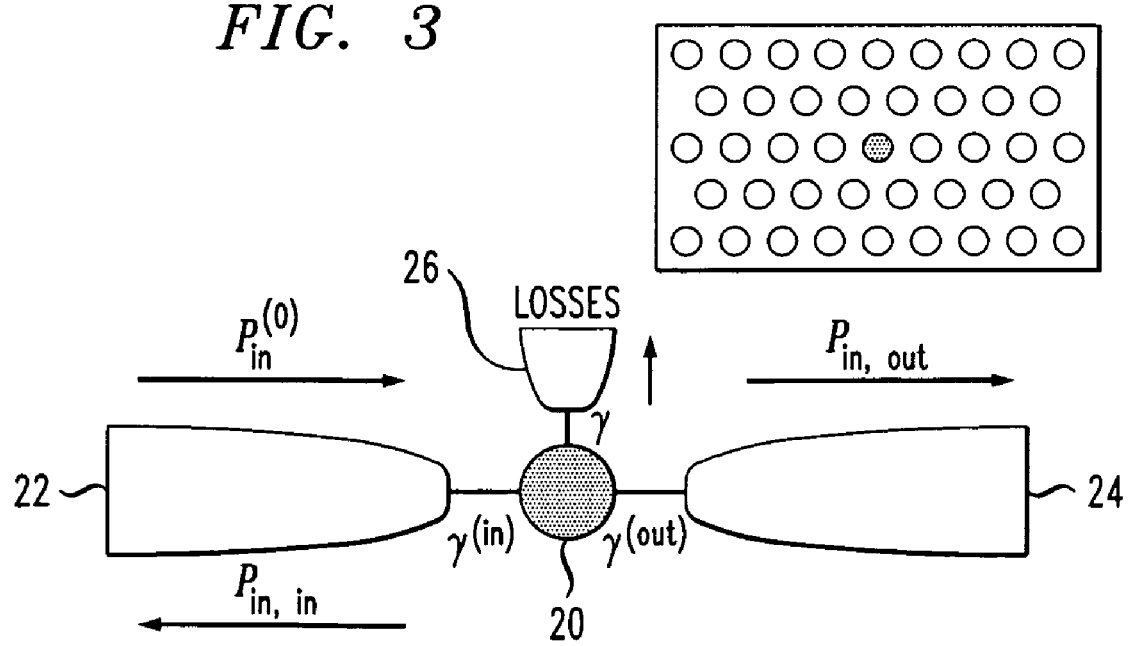
FIG. 3 is a model of a resonant optical sensor comprising a single elementary resonator.

FIG. 3 represents a simplified arrangement of the model of FIG. 2, in this case with a single resonator 20 disposed between input waveguide 22 and output waveguide 24. As before, the input power spectrum is defined as $P_{in}^{(0)}$, the transmitted spectrum is defined as $P_{in, out}$, and the reflected spectrum is defined as $P_{in, in}$. In as much as the FIG. 3 embodiment is a simplified form (i.e., a single resonance), the coupling coefficient between input waveguide 22 and resonator 20 can be denoted as $\gamma^{(in)}$, without requiring a subscript to define the specific resonator. Similarly, the coupling coefficient between resonator 20 and output waveguide 24 is denoted as $\gamma^{(out)}$. As discussed above in association with FIG. 2, the intrinsic losses associated with this single-resonator structure are defined by the constant $\gamma$, illustrated in FIG. 3 as coupled into the virtual output waveguide 26. The inset in FIG. 3 shows an exemplary physical arrangement that can be investigated with this simplified model: a photonic crystal waveguide with a built-in resonator. Using the above Breit-Wigner formula, the resonant transmission peak for the arrangement of FIG. 3 can be defined as follows:

$$P_{in,out} = P_{in}^{(0)} \frac{\gamma^{(in)} \gamma^{(out)}}{(\lambda - \lambda_1)^2 + 1/4(\gamma^{(in)} + \gamma^{(out)} + \gamma)^2},$$

where $\gamma$ is the intrinsic loss (i.e., the fixed loss associated with material properties) of the resonator and $\lambda_1$ is the eigenvalue associated with the single resonator, as shown in FIG. 3. In a similar fashion, the reflected power $P_{in,in}$ is determined by the following form:

$$P_{in,in} = P_{in}^{(0)} - P_{in,out} - P_{in,loss}$$

$$= P_{in}^{(0)} \frac{(\lambda - \lambda_1)^2 + 1/4(\gamma^{(in)} - \gamma^{(out)} - \gamma)^2}{(\lambda - \lambda_1)^2 + 1/4(\gamma^{(in)} + \gamma^{(out)} + \gamma)^2}.$$

The Q-factor of the transmission and reflection resonances is defined by the following:

$$Q = \frac{\lambda_1}{2(\gamma^{(in)} + \gamma^{(out)} + \gamma)},$$

where it cannot exceed the intrinsic Q-factor:

$$Q_{int} = \frac{\lambda_1}{2\gamma}.$$

Figure 4:
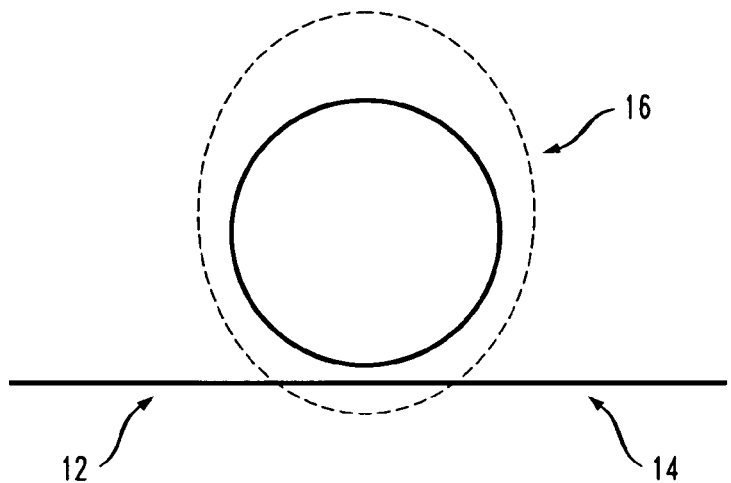
FIG. 4 illustrates an exemplary ring resonator.

One exemplary type of resonant optical sensor that is frequently employed is the ring resonator, of the form shown in FIG. 4. This resonator can be modeled by the resonator of FIG. 3, in which there is only a single coupling coefficient so that, for example, one may assume $\gamma^{(out)}=0$.

Figure 5:
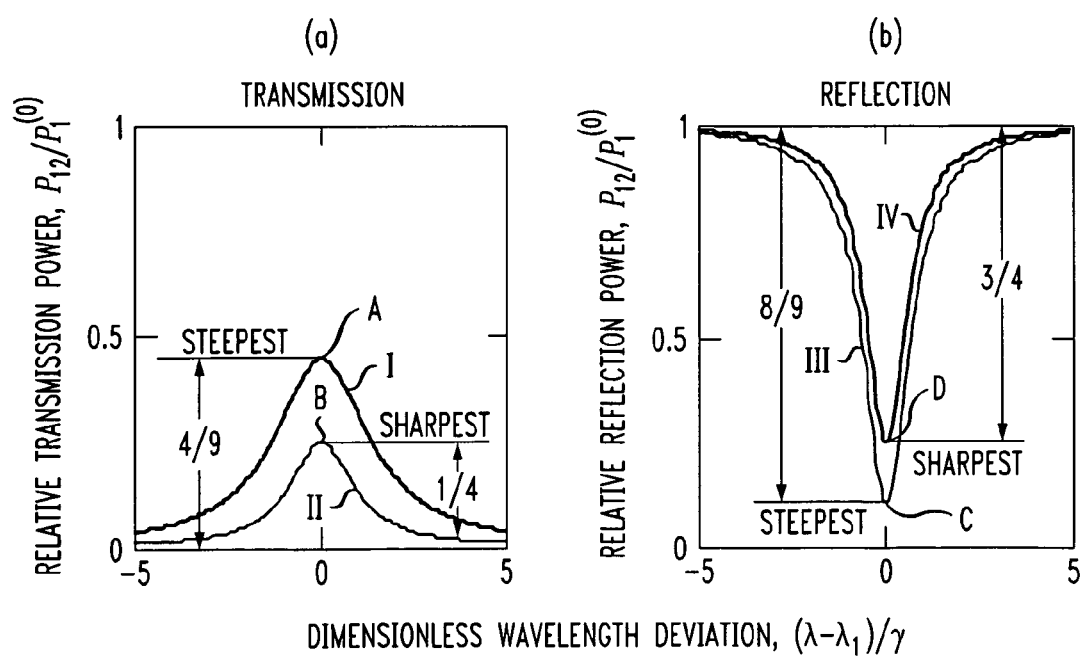
FIG. 5 contains plots slope and sharpest peak values for transmission spectra (FIG. 5(a)) and reflection spectra (FIG. 5(b)).

With these various relations in mind, the optimization of the sensor in accordance with the present invention follows by first realizing that the parameters $\lambda_1$, $\gamma^{(in)}$, and $\gamma^{(out)}$ are all variable and can therefore be modified to provide optimum values, since they are modified by changing the geometry of the resonator itself, for example, by changing the distance between the input/output waveguides and the resonator cavity. The parameter $\gamma$ is defined as a constant, since it defines the intrinsic loss of the sensor. The following calculations thus allow the optimized transmission and reflection resonant peaks to be determined, as depicted in FIGS. 5(a) and (b), respectively.

In particular, the shape of the resonance in the sensor spectrum depends upon the wavelength ($\lambda$) of the light passing through the sensor, as well as the variable quantities of the resonator eigenvalue ($\lambda_1$ for the single resonance structure) and coupling coefficients ($\gamma^{(in)}$, $\gamma^{(out)}$), as described above. Thus, in accordance with the present invention, the optimization of the sensitivity based upon the maximum slope ($S_{max}$) of the spectrum is defined by the following relation, the first derivative of the spectrum:

$$S_{max} = \max_{\lambda, \gamma^{(in)}, \gamma^{(out)}} \left( \frac{dP(\lambda, \gamma^{(in)}, \gamma^{(out)})}{d\lambda} \right).$$

Similarly, the sharpest peak in the sensor's spectrum (denoted as $\Theta_{max}$) can be determined from its second derivative, as follows:

$$\Theta_{max} = \max_{\lambda, \gamma^{(in)}, \gamma^{(out)}} \left( \frac{d^2 P(\lambda, \gamma^{(in)} \gamma^{(out)})}{d\lambda^2} \right).$$

Applying the above relations to the transmission resonant peak formula as presented above, the 'steepest' slope in transmission ($S_{max}$), labeled as curve I of FIG. 5(a), is achieved at the following value:

$$\lambda = \lambda_1 \pm \frac{\sqrt{3}}{2} \gamma,$$

and $$\gamma^{(in)} = \gamma^{(out)} = \gamma,$$

which corresponds to an overall resonator Q-factor equal to ½ $Q_{int}$ and a relative power peak height (defined as $P_{in,out}/P_{in}^{(0)}$) of 4/9, shown as point A in curve I of FIG. 5(a). The 'sharpest' peak in transmission ($\Theta_{max}$), labeled as point B along curve II in FIG. 5(a), is achieved at the following value:

$$\gamma^{(in)} = \gamma^{(out)} = \frac{1}{2}\gamma,$$

again corresponding to an optimum transmission Q-factor equal to ½ $Q_{int}$ and in this case a relative power peak height of ¼, as shown in FIG. 5(a).

The same evaluations can be made for the maximum slope and resonant peak in reflection spectrum (using the above derivative relations), where in this case the steepest slope ($S_{max}$) in the reflection spectrum is defined by:

$$\lambda = \lambda_1 \frac{\sqrt{3}}{4} \gamma, \quad \gamma_{in}^{(out)} = 0,$$

and $$\gamma_{in}^{(in)} = 1/2\gamma,$$

which corresponds to Q=⅔ $Q_{int}$ and a relative peak height of 8/9, shown by point C in curve III of FIG. 5(b). The sharpest peak $\Theta_{max}$, labeled as point D in FIG. 5(b), is defined as follows:

$$\gamma^{(out)} = 0; \quad \gamma^{(in)} = \frac{1}{3}\gamma,$$

which corresponds to an optimum reflection Q-factor, $Q_{opt,R}$ equal to ¾ $Q_{int}$, and a relative power peak height of ¾, as shown by curve IV in FIG. 5(b).

It is also possible to compare the values of the maximum possible slope and sharpness values that can be achieved in transmission and reflection. For transmission:

$$\max\left( \frac{dP_{in,out}}{d\lambda} \right) = \frac{P_{in}^{(0)}}{3^{3/2}\gamma} = \frac{0.192}{\gamma} P_{in}^{(0)},$$

slope $$\max\left( \frac{d^2 P_{in,out}}{d\lambda^2} \right) = \frac{P_{in}^{(0)}}{2\gamma^2} = \frac{0.5}{\gamma^2} P_{in}^{(0)},$$

steepness, and for reflection:

$$\max\left(\frac{dP_{in,in}}{d\lambda}\right) = \frac{4P_{in}^{(0)}}{3^{3/2}\gamma} = \frac{0.770}{\gamma}P_{in}^{(0)},$$

slope $$\max\left(\frac{d^2 P_{in,in}}{d\lambda^2}\right) = \frac{27 P_{in}^{(0)}}{8\gamma^2} = \frac{3.375}{\gamma^2}P_{in}^{(0)},$$

steepness.

From the above, it is clear that sensing in reflection is more favorable than sensing in transmission. Indeed, the maximum possible steepness and sharpness of the reflection peak is, respectively 4 and 6.75 times greater than the same parameters of the transmission peak.

The results obtained in accordance with the present invention are particularly useful for a simple visual analysis of experimentally universal values that are independent of the system parameters. For example, for the transmission spectrum, a peak with a surprisingly 'small' relative height of ¼ is the sharpest possible peak that can be produced.

While the above relations have been explored for the simple single resonator case, the results can be generalized to the n-coupled resonator model. In particular, numerical simulations have shown that the maximum steepness and sharpness of the reflection spectrum for a double-resonance sensor cannot exceed that determined for the single-resonance model. In particular, when more than a single resonance is included within the system, the coupling coefficients $\delta_{mn}$ between resonators m and n are also variables to be considered when developing the optimized arrangement. Other variables to be considered are the eigenvalues $\lambda_n$ associated with each resonator. Numerical simulations for the case of two coupled resonances with intrinsic loss $\gamma$ have found that the slope reaches a maximum for $\gamma^{(in)}=\gamma^{(out)}>>\gamma$ (the intrinsic loss). In other words, the input waveguide needs to be strongly coupled to the output waveguide so as to be able to ignore the intrinsic losses. The sharpest peak in the double resonance model maintains this same condition, while also satisfying the relation $\gamma^{(in)}=\gamma^{(out)}>>|\lambda-\lambda_1|$.

Indeed, while the invention has been particularly described and shown with reference to specific embodiments, it should be understood by those skilled in the art that various changes in form and detail may be made therein without departing from the spirit and scope of the invention as defined by the claims appended hereto.

What is claimed is:

1. A resonant optical sensor comprising
   an input waveguide, for receiving an optical sensing signal at a wavelength $\lambda$;
   a resonating optical device coupled to the output of the input waveguide for allowing the optical sensing signal to propagate therethrough and creating a resonant spectrum as a function of the ambient medium of the sensor, with a coupling coefficient between the input waveguide and the resonating optical device defined as $\gamma^{(in)}$, the resonating optical device exhibiting a fixed, intrinsic loss $\gamma$ and associated intrinsic Q-factor $Q_{int}$; and
   an output wave guide coupled to the output of the resonating optical device for receiving the resonant transmission spectrum, with a coupling coefficient between the output waveguide and the resonating optical device defined as $\gamma^{(out)}$, the resonant optical sensor being optimized with respect to sensitivity in measuring changes in the ambient medium by adjusting one or more variable parameters from a predefined set of variable parameters to create a resonant spectrum output signal having a maximum slope and/or sharpest peak, regardless of Q-factor.

2. A resonant optical sensor as defined in claim 1 wherein the set of variable parameters includes: the geometries of the input waveguide, the resonating optical device and the output waveguide; the spacings and physical couplings therebetween; refractive index values of the input waveguide, the resonating optical device, the output waveguide and the areas therebetween.

3. A resonant optical sensor as defined in claim 1 wherein the sensor exhibits a maximum slope in its associated spectra by modifying its coupling coefficients and eigenvalues in association with the following relation:

$$S_{max} = \max_{\lambda,\gamma^{(in)},\gamma^{(out)}}\left(\frac{dP(\lambda, \gamma^{(in)}, \gamma^{(out)})}{d\lambda}\right).$$

4. A resonant optical sensor as defined in claim 1 wherein the sensor exhibits a maximally sharp peak in its associated spectra by modifying its coupling coefficients and eigenvalues in association with the following relation:

$$\Theta_{max} = \max_{\lambda,\gamma^{(in)},\gamma^{(out)}}\left(\frac{d^2 P(\lambda, \gamma^{(in)}, \gamma^{(out)})}{d\lambda^2}\right).$$

5. A resonant optical sensor as defined in claim 1 wherein the resonating optical device exhibits a single resonance peak.

6. A resonant optical sensor as defined in claim 5 wherein the sharpest, single resonance peak in the transmission spectrum is associated with a Q-factor of approximately ⅔$Q_{int}$.

7. A resonant optical sensor as defined in claim 5 wherein the steepest slope, single resonance peak in the transmission spectrum is associated with a Q-factor of approximately ½$Q_{int}$.

8. A resonant optical sensor as defined in claim 5 wherein the sharpest, single resonance peak in the reflection spectrum is associated with a Q-factor of approximately ¾$Q_{int}$.

9. A resonant optical sensor as defined in claim 5 wherein the steepest slope, single resonance peak in the reflection spectrum is associated with a Q-factor of approximately ⅔$Q_{int}$.

* * * * *